United States Patent [19]

Shane

[11] Patent Number: 5,358,521

[45] Date of Patent: Oct. 25, 1994

[54] MULTIPLE-LAYER PROSTHESIS IMPLANT WITH TISSUE TACTILITY

[76] Inventor: Fred Shane, 205 E. Harmon, Apt. 803, Las Vegas, Nev. 89109

[21] Appl. No.: 861,522

[22] Filed: Apr. 1, 1992

[51] Int. Cl.$^5$ .......................... A61F 2/12; A61F 2/54
[52] U.S. Cl. ........................................ 623/8; 623/66
[58] Field of Search ..................... 623/8, 7, 11, 66

[56] References Cited

U.S. PATENT DOCUMENTS

| | | | |
|---|---|---|---|
| 3,934,274 | 1/1976 | Hartley, Jr. | 623/8 |
| 4,298,998 | 11/1981 | Naficy | 623/8 |
| 4,650,487 | 3/1987 | Chaglassian | 623/8 |
| 4,731,081 | 3/1988 | Tiffany et al. | 623/8 |
| 4,790,848 | 12/1988 | Cronin | 623/8 |
| 4,944,749 | 7/1990 | Becker | 623/8 |
| 5,092,882 | 3/1992 | Lynn et al. | 623/8 |

Primary Examiner—Randall L. Green
Assistant Examiner—Dinh X. Nguyen

[57] ABSTRACT

A multi-layer prosthesis simulates tissue tactility by structuring the plurality of layers of material making up the prosthesis to include lubricant coating between the layers. It is the plurality of layers and the lubricity of their movement which contributes greatly to the tactile simulation of human tissue. Present in the prosthesis is a ballast lumen which moves freely and contributes mass and motility to the prosthesis. The prosthesis finds ready use in the augmentation or restructuring of the human breast as well as in cosmetic modification of other portions of the anatomy as, for example, the chin, the pectorals, the calf muscles, etc.

24 Claims, 2 Drawing Sheets

MULTIPLE-LAYER PROSTHESIS IMPLANT WITH TISSUE TACTILITY

BACKGROUND

1. Technical Field of the Invention

The invention relates to a prosthetic implant for supplementing existing body tissue contours. Thus the implant might be used to augment the contours of a person's breasts, pectorals, chin, calves, and the like. In particular, the invention relates to a prosthesis made up of multiple layers of lubricated material which simulate the tactility and motility of natural body tissues when the implant has been placed within a person's body.

2. Prior Background Art

Tissue simulating, body implants are probably most readily associated in people's minds with mammary prosthesis. Because of this ready association, the invention will be disclosed in terms of a mammary implant to be used for purposes of breast reconstruction or augmentation. However, it is emphasized that this is done for purposes of exposition only. No attempt at limiting the use of the invention is intended. The teachings disclosed herein are applicable to tissue simulating implants of various types including those implanted within a person's chin, pectoral muscles, calves, and the like.

Most tissue simulating prosthesis provide a container, often referred to as a sac or a lumen in the prior art. The lumens are generally inflated with a liquid or gel to add volume to the prosthesis when positioned within a person's body. Tiffany in U.S. Pat. No. 4,731,081 discloses that the single lumen prosthesis is the most realistic. However, fluid filled lumens all display a problem in that they appear to be susceptible to damage and subsequent leakage of the fill material into the body tissues of the person in which the implant is made. The recent notoriety of persons allegedly suffering bodily harm as a result of a leakage of silicone gel from implanted prosthesis exemplifies the concern with which effective prosthesis design must be approached.

Tiffany notes that the lumen often develops a crease causing opposite walls of the lumen to bear on and frictionally remove material from each other. If the removal of material becomes sufficient, the wall is ruptured and the inflating fluid leaks into the body tissues. To inhibit such frictional wear, Tiffany adds a lubricant to the inflating fluid used to inflate the lumen. The lubricant is chosen so as not to separate or settle out from the inflating liquid. Tiffany teaches that the lubricant shall be less than 70 percent of the total of the liquid-plus-lubricant within the lumen, only 5 to 10 per cent by weight.

In U.S. Pat. No. 3,934,274, Hartley, Jr. teaches of a two lumen prosthesis. The inner lumen in anchored to the walls of the outer lumen. As the inventor Becker, referred to hereinafter, will later note, the placement of one lumen within another, wherein each lumen has an anchor point which places a limitation on the mobility of one lumen to move within the other, creates a center for high concentration of shearing forces. As one lumen moves within the other, flexing about its anchor point, leaks frequently occur.

Tiffany places 100–300 cc of silicone gel within his inner lumen, 75–125 cc of saline solution in his outer lumen. He teaches that the outer lumen may be semi-permeable to permit an exchange of fluid between the sac and body tissue. Leakage of silicone gel into the body tissues as well as the insertion of the prosthesis within the body-tissues often causes capsular contracture of the tissue about the implant. The implant in turn contracts so as to assume a spherical shape. This spherical contracture usually results in an unrealistic tissue outline which is rigid and tense. Hartley teaches that some of the saline solution may be removed from the outer sac so as to decompress the sac to defeat the spherical contracture of the prosthesis.

Chaglassian, in U.S. Pat. No. 4,650,487, builds upon the Hartley prosthesis in that he provides three lumens, as opposed to Hartley's two. All lumens are anchored together and thus suffer the sheer force, potential for damage noted above. The outermost lumen in Chaglassian's prosthesis is deflatable so as to relieve the effects of spherical contracture. The innermost lumen is a high profile container intended to provide high projection of the breast.

Another inventor seeking to provide high projection of the prosthesis augmented breast is Cronin. In U.S. Pat. No. 4,790,848, Cronin teaches a two lumen prosthesis. However, unlike the earlier prosthetic devices noted above, Cronin teaches that the inner lumen shall be free floating; it must be small relative to the outermost lumen having only 25 to 60 per cent of that volume of that outer lumen; and, it must be spherical in shape. Cronin emphasizes the spherical shape of the inner lumen. He is critical of earlier implants in which the inner lumen has the same general shape and approximate size as the outer lumen. The reasons given for Cronin's criticism are that an inner lumen having the same general shape and approximate size of the outer lumen is limited in motion and maintains no projection of the breast.

A two lumen, free floating structure is taught by Becker is U.S. Pat. No. 4,944,749. Through a unique valving arrangement, disclosed by Becker, both inner and outer lumens may be inflated after insertion within the body of the patient. Becker inflates his outer lumen with 40–50 cc of a viscous gel. Following Tiffany's lead, Becker notes that the gel has desirable lubricating characteristics.

However, he treats the lubrication aspects as an incidental benefit since the gel, 40–50 cc in volume, functions primarily as an inflating fluid for the outer lumen.

In its varying aspects, the prior art discloses an awareness of implant prosthesis which make use of multiple lumens. However, the prior art requires that each of the lumens making up a given prosthesis shall be inflated with a significant volume of fluid since each of the prior art prostheses depends primarily on the inflating fluid to produce desirable tactility and motion. None of the prior art disclosed relies on a multiplicity of lubricated walls wherein the plurality of walls and the lubricity of relative motion among the plurality of walls imparts the desired tactility and movement of natural body tissue when a prosthesis, so structured, is implanted in a patient's body.

SUMMARY DESCRIPTION OF THE INVENTION

The invention is a multiple-layer prosthesis. Its structure provides the tactility and motility of natural body tissue when the prosthesis is implanted in the body. The prosthesis is a multiple lumen prosthesis. There is a first, ballast lumen enclosed within a second lumen. Each of the lumens has flexible exterior and interior walls. The interior walls define an interior void. The ballast lumen is enclosed within the interior void of the second lumen.

There is a first coating of lubricant on the interior walls of the second lumen. There is a second coating of lubricant on the exterior walls of the ballast lumen. The first coating and the second coating of lubricant inhibit direct contact of the exterior walls of the ballast lumen with the interior walls of the second lumen. Included in the prosthesis are means coupling the first and second coatings of lubricant for the purpose of renewing the lubricant by redistributing lubricant within the two coatings. The means for renewing the first and the second coatings of lubricant comprises the ballast lumen itself. The ballast lumen has its interior void filled with fluid of a selected density.

The flexible interior and exterior walls of the first and second lumens comprise a material selected in combination with the multiplicity of the walls and the lubricity of relative motion among the walls to impart the tactility and movement of natural body tissue when the prosthesis is implanted in a patient's body. The relative movement is induced, in part, by movement of the ballast lumen within the second lumen.

In a preferred embodiment of the invention, there are a multiplicity of additional lumens, third through N'th, where N represents a selected maximum number of lumens. Each of the third through N'th lumens has flexible exterior and interior walls defining an interior void in each of the lumens. The interior walls of the third through N'th lumens has the first coating of lubricant thereon; and the exterior walls of the second through (N−1)'th lumens has the second coating of lubricant thereon.

Each the third through N'th lumens is graduated in size to accept, and accepts, its preceding one of the second through (N−1)'th lumens within its interior void. The size gradation of lumens is sufficient to permit free relative motion between the interior walls of a given one of said third through N'th lumens and the exterior walls of its preceding one of said second through (N−1)'th lumens enclosed within the interior void of that given one of the lumens. The prosthesis is, in essence, a sac-en-sac assembly of the first through N'th lumens.

There are means coupling the first and the second coatings of lubricant between adjacent interior and exterior walls of the multiplicity of additional lumens for purposes of renewing the first and the second coatings.

The means for renewing the first and the second coating of lubricants comprises the adjacent interior and exterior walls of the multiplicity of additional lumens. Free relative motion between the walls brings the first and the second coating of lubricant into repeated, moving contact. Thus, lubricant within the first and the second coatings is exchanged and redistributed.

Alternative to or in conjunction with the moving ballast lumen, the means for renewing the first and the second coatings of lubricant further comprises an interstitial, distribution layer of lubricant, immiscible in the first and the second coatings of lubricant. The distribution layer of lubricant is generally located between the first and the second coatings of lubricant, further inhibiting direct contact of the exterior walls of the ballast lumen with the interior walls of the second lumen, and further redistributing lubricant in the first and second coatings of lubricant along boundaries at which the distribution layer of lubricant moves relative to the first and the second coatings.

An alternative embodiment of the invention includes the first and second lumens and further comprises a plurality of tissue simulating walls each coupled to a first wall of the second lumen. Each one of the plurality of tissue simulating walls is concentric, one to the other, the tissue simulating walls being graduated in size. Each one of the tissue simulating walls, so coupled to the second lumen, defines an interior void. Each one of the tissue simulating walls has thereon at least one of the first and the second coatings of lubricant for inhibiting direct contact between adjacent tissue simulating walls within each interior void so defined.

The alternative prosthesis further comprises means coupled to each of said coatings of lubricant for redistributing lubricant on the tissue simulating walls.

The means for redistributing lubricant on the tissue simulating walls comprises the ballast lumen. The free movement of the ballast lamen within the second lumen communicates motion to the tissue simulating walls whereby the lubricant coatings are brought into repeated moving contact so that lubricant within the lubricant coatings is exchanged and redistributed.

DETAILS OF BEST MODE FOR CARRYING OUT THE INVENTION

Figure 1:
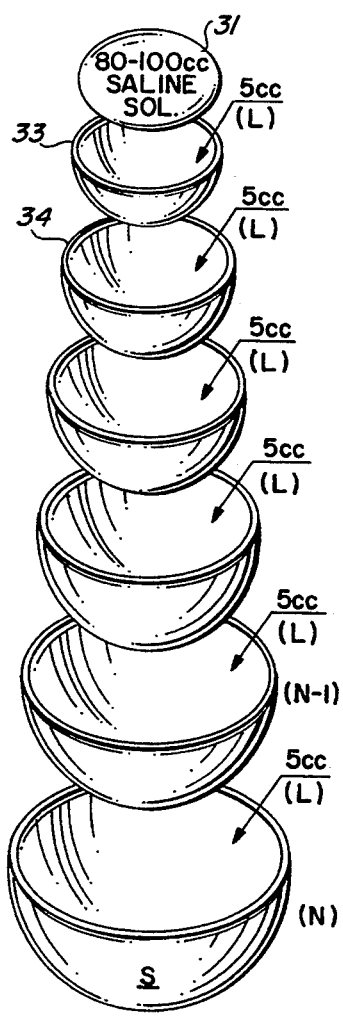
FIG. 1 is an exploded assembly drawing of the multilayer prosthesis implant disclosed herein. The multiplicity of lubricated layers simulates the tactility of body tissue.

For purposes of promoting an understanding of the principles of the invention, reference will now be made to the embodiments illustrated in the drawings and specific language will be used to describe same. It will nevertheless be understood that no limitation of the scope of the invention is thereby intended, there being contemplated such alterations and modifications of the illustrated device, and such further applications of the principles of the invention as disclosed herein, as would normally occur to one skilled in the art to which the invention pertains.

In the embodiments of the invention disclosed herein, a fluid filled lumen will contribute most of the bulk of the innovative prosthesis. When the prosthesis is for purposes of breast augmentation or reconstruction, the single lumen may be expected to have 80–100 cc of, for example, saline solution. Breast prosthesis with 180–300 cc of fluid are not unknown.

In addition to the fluid filled lumen, a plurality of thin walled layers of flexible material, each layer being lubricated so as to move easily, one with respect to the other, is included as an integral part of the prosthesis. The multiplicity of material layers and the lubricity of motion contribute greatly to the simulation of body tissue tactility when the prosthesis is emplaced in the patient's body.

A first, presently preferred embodiment of the invention is illustrated in the exploded assembly drawing of FIG. 1. Here is shown a plurality of thin-walled, flexible sacs or lumens. Each succeeding lumen has its diameter slightly larger than that of its predecessor. Each lumen is inserted in the next larger diameter lumen. This produces a "sac-en-sac" nested arrangement Each lumen is free to move within its containing lumen. Lumen 31, containing saline solution, is generally hereinafter referred to as the ballast lumen since most of the mass of the device is contributed by this lumen. Ballast lumen 31 is inserted into lumen 33 with approximately 5 cc of lubricant. Lumen 33 is then sealed.

The 5 cc of lubricant within lumen 33 coats the interior walls of lumen 33 and the exterior walls of ballast lumen 31. Since lumen 33 is larger, by approximately by ⅛ to ¼ of an inch then ballast lumen 31, lumen 31 may move freely within lumen 33, contacting all interior surfaces of lumen 33 and inhibiting any tendency for the occurrence of creases in the walls of lumen 33, as well as the walls of all other enveloping lumens. As lumen 31 moves, forces are exerted through all the enveloping walls and layers of lubricant to bring all walls into creaseless alignment.

Lumen 33, with its enclosed ballast lumen 31 is next inserted into lumen 34 with an additional 5 cc of lubrication. As before, the lubrication coats the interior walls of lumen 34 and the exterior walls of lumen 33 so that lumen 33, with its enclosed lumen 31 is free to move within lumen 34, which is slightly larger than lumen 33, by, for example, an ⅛ to ¼ of an inch. Lumen 34 is thereafter sealed.

The assembly procedure continues until a selected number, N, of lumens has been placed in the sac-en-sac arrangement. The lumens are made of flexible, biocompatable materials, such as a silicone elastomer. Ballast lumen 31 is preferably filled with a physiologic fluid, e.g., a normalsaline solution.

All lumen materials are chosen, as well, for the tactile impression gleaned from the implanted prosthesis. Newer silicone materials coming onto the market have the body tissue tactility suggested by latex, yet, unlike latex, are biocompatible.

The outermost lumen, the N'th lumen in the sac-en-sac structured prosthesis of FIG. 1, preferably has a textured, biocompatible surface S so as to disorganize scar tissue which forms around the implanted prosthesis. Such "disorganization" prevents the massing of scar tissue and the subsequent contracture of the implant. Scar induced contracture can cause a prosthesis to compress to a minimum volume envelop, becoming spherical in shape, and tense and rigid to the touch.

The notation in FIG. 1 of the addition of 5 cc of lubricant to each of the lumens enveloping ballast lumen 31 emphasizes that the invention does not depend upon these enveloping lumens being filled or inflated to near capacity. Sufficient lubricant is injected into each enveloping lumen, e.g., lumens 33, 34, . . . , N, to assure that the interior walls of an enveloping lumen and the exterior walls of an enveloped lumen are coated with lubricant. The lubricant is selected to coat these walls as well as to fill any pores in the wall surfaces.

As will be disclosed hereinafter, a second lubricant, having selected density and viscosity characteristics with respect to that lubricant coating the wall surfaces, will form a laminar, lubricant boundary between wall-covering-coatings of lubricant to, in a sense, lubricate the lubricant at the walls of the lumens.

Figure 2:
FIG. 2 is a cross sectional view of a prior art, single lumen breast implant.
Figure 3:
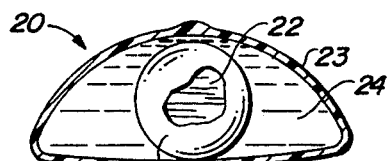
FIG. 3 is a cross sectional view of a prior art breast implant which includes a separate, inflated lumen within the outer, mammary shaped lumen.

FIGS. 2 and 3 illustrate prior art prosthetic devices for augmenting or restructuring a breast. In the illustration of FIG. 2, prior art implant 10 comprises a silicone rubber lumen 10 which is filled with a gel, most frequently silicone. Silicone gel-filled, mammary prostheses have come under fire recently in that leakage of the silicone gel from lumen 11 into a woman's body has been alleged to produce severe bodily dysfunction. It is supposed that lumen 11 develops a crease in its wall after implantation. Frictional wearing caused by one wall bearing on another at the point of creasing is thought to cause a rupture of the sac and allow the silicone gel 12 to leak into the woman's body.

A somewhat similar prior art implant 20 is shown is FIG. 3. Here, in addition to an exterior lumen 23 which is filled with either a gel or a liquid 24, a second, internal lumen 21 is provided. Lumen 21 contains a silicone gel 22 and has a shape, either spherical or conical, chosen to enhance the projection of the augmented or reconstructed breast. In those prior art prosthesis in which the inner lumen 21 is anchored at a contact point 26 within outer lumen 23, stress induced fractures frequently appear at contact point 26. These fractures in turn lead to leakage of silicone gel or other fluids from lumens 21 and/or 23.

Figure 4:
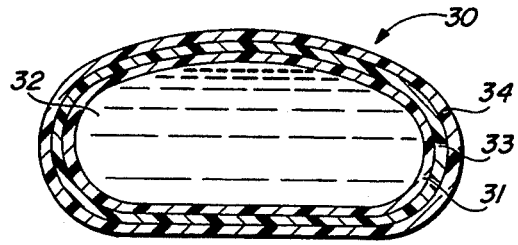
FIG. 4 is a cross sectional view of a multi-layer prosthesis implant as taught herein. A single ballast lumen is filled with fluid to an extent generally approximating the volume desired for the overall transplant.

In FIG. 4 is shown a cross sectional view of a mammary prosthesis 30 comprised of three lumens 31, 33, and 34 assembled sac-en-sac in the manner disclosed with reference to FIG. 1. The implant 30 has three layers of thin walled material above the saline solution contained within lumen 31. Each lumen, 31 and 33, is free to move within its enclosing lumen. However, in the scale of the drawing of FIG. 4, the ability of the lumens to so move is not readily discernible.

Figure 5:
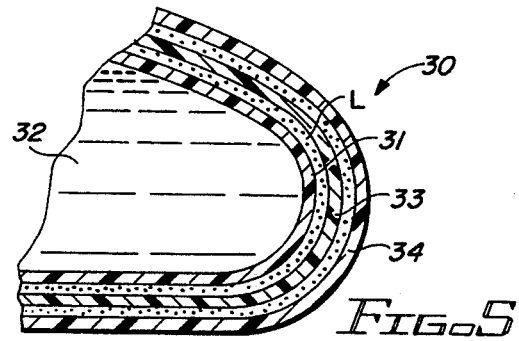
FIG. 5 is an enlargement of the cross sectional drawing of the FIG. 4 showing clearly that the prosthesis is made of a plurality of lumens, one within the other in a sac-en-sac arrangement, each lumen being separated by a layer of lubricant and, the lumens being graduated in size to permit free movement of one lumen in another.

The larger scale of the drawing of FIG. 5 indicates that the interior and exterior walls, separating adjacent and enclosed lumens, are coated with lubricant L. The coatings of lubricant L provide the lubricity which permits the walls of lumens 31, 33, and 34 to move adjacent to and with respect to each other in a manner which simulates the tactility and motility of body tissue.

Figure 6:
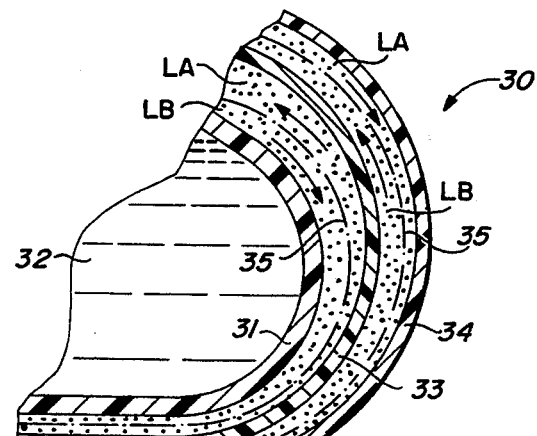
FIG. 6 is a further enlargement of a portion of the cross sectional drawing of FIG. 5 with arrows indicating the relative movements of one lumen within another and the relative movement of the respective coatings of lubricant, one in relationship to another as the adjacent walls of the lumens move relative to each other.

A further increase in scale is provided is FIG. 6. Here, ballast lumen 31 is shown by the arrows to be moving in a direction relatively opposite to that of its enclosing lumen 33. This relatively opposite movement of the walls of the two lumens produces a laminar-like boundary 35 between adjacent coatings of lubricant LA and LB, since the lubricant tends to adhere to the wall of the lumen with which it is in contact, and those lumen walls are moving oppositely one to the other. In a preferred embodiment of the invention, the laminar boundary 35 between lubricant coatings LA and LB will be enhanced by an additional lubricant layer which is immiscible in either one of lubricant coatings LA or LB. This arrangement is shown in the further enlargement of FIG. 7.

Figure 7:
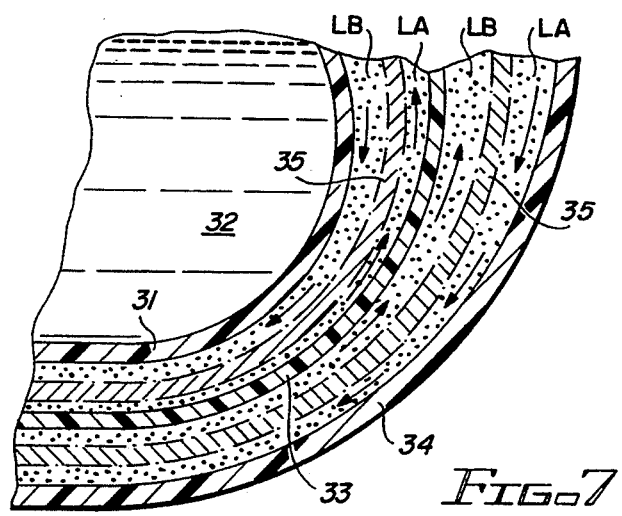
FIG. 7 is a further enlargement of the cross sectional drawing of FIG. 6 showing the introduction of an immiscible lubricant having a selected density differing from that of the lubricant coatings indicated earlier. The immiscible lubricant layer lies between layers of lubricant coating and "lubricates the lubricant" and provides an exchange of lubricant coatings between adjacent layers.

In the drawing of FIG. 7 there is a coating of lubricant LB adjacent to the exterior wall of lumen 31. Similarly, there is a coating of lubricant LA adjacent the interior wall of lumen 33. The lubricant of coatings of LA and LB has been selected to cover the wall surfaces of the lumens and to fill any pores in the material for which the lumens are fabricated.

A second lubricant within laminar boundary 35 was injected with the lubricant L, forming coatings LA and LB, at the time that ballast lumen 31 was inserted within lumen 33 and lumen 33 was sealed. The lubricant within laminar boundary 35 was chosen to be immiscible within the lubricant of coatings LA and LB. Further, the density and viscosity of the lubricant making up coating LA and LB differs from that in the lubricated boundary layer 35. This lubricated boundary layer 35 is made up of lubricant LC which in effect lubricates the lubricant coatings LA and LB.

The movement of lumens one within the other, for example, lumen 31 within lumen 33, renews the lubricant coating on the walls of these lumens by redistributing lubricant. Thus, if there is no lubricant LC between lubricant coating LA and LB, there is a tendency for lubricant to move across boundary 35, in either direction, to and from coatings LA and LB. The moving contact of the boundary layer coatings LA and LB contribute to the redistribution of lubricant on and about the surfaces of the lumens.

In the case in which a second lubricant LC is introduced, there is a movement of lubricant LA and LB along the boundary layer 35 with lubricant layer LC and occasionally through lubricant LC. Again, the relative movement of the various layers of lubrication contributes to a redistribution of the lubricant and a renewal of the coatings on the surfaces of the various lumens.

Returning now to the illustration of FIG. 4, the mass of the prosthesis is provided, in general, by the mass of saline fluid 32 filling ballast lumen 31. Each additional lumen 33 and 34 provides a plurality of layered materials, each layer of which is lubricated. The free movement of one lumen within another and the ease of movement provided by the lubricated surfaces lends the prosthesis the tactility and motility of body tissue when it is implanted at a site within a person's body. The size of the prosthesis, its tactility, and motion depend upon the number of layers of material and lubricity of their motion and the mass/volume of the ballast lumen 31.

Figure 8:
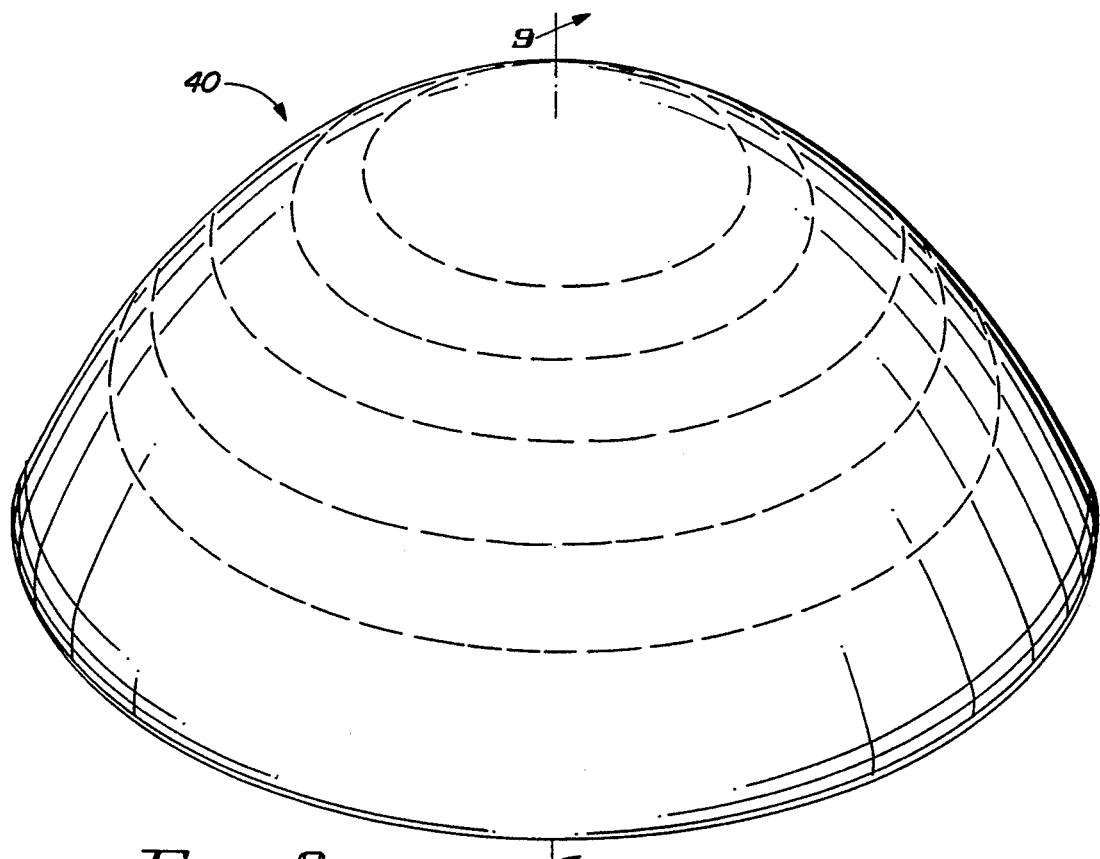
FIG. 8 illustrates an alternate embodiment of the multi-layer prosthesis implant.
Figure 9:
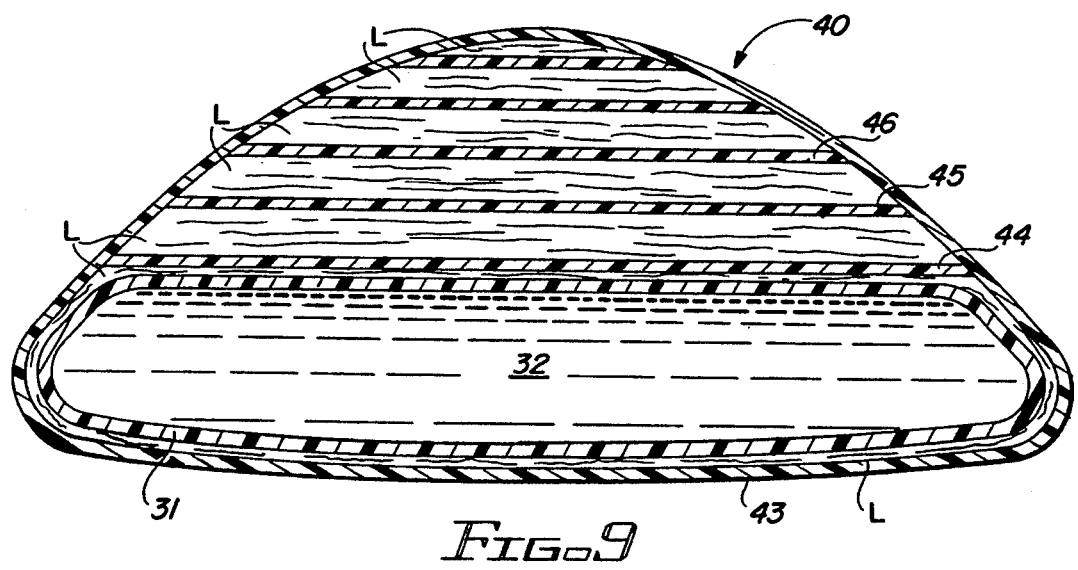
FIG. 9 is a cross sectional drawing of the prosthesis of FIG. 8 showing two lumens, the innermost lumen being filled with a ballast fluid and the outermost lumen having a plurality of interior walls, each of which is lubricated to provide a tissue like tactility when the implant is embedded within the body.

An alternative structure for the multi-layer prosthesis is shown in FIGS. 8 and 9. In FIG. 8, mammary implant 40 is shown. On the surface of implant 40 is seen the outlines of the interior structural walls of the implant.

As best seen in the sectional drawing of FIG. 9, implant 40 is comprised of an exterior lumen 43 having enclosed therein a free moving lumen 31 which is fluid filled with, for example, saline solution 32. A series of interior walls are affixed to lumen 43, for example, walls 44, 45, and 46. Each of these walls is fastened to lumen 43 by means well known for those in the prior art, for example, by heat welding. As each wall is attached to the interior wall of lumen 43, proceeding from the smallest in diameter to the largest, a small lumen is formed which is provided with a coating of lubricant L. Thus, as each wall is added, a new lumen is provided; and each layer or wall of these individual lumens is lubricated. Thus, the multi-layered structure advocated by this disclosure is again provided. Each of the layers is lubricated. And, the multiplicity of the layers and lubricity of their movement, in conjunction with the free movement of the ballast lumen, contributes tactility and motility to the prosthesis which simulates body tissues when implanted in a human body.

What has been disclosed is a multi-layer prosthesis which simulates tissue tactility by structuring the plurality of layers of material making up the prosthesis to include lubricant coating between the layers. It is the plurality of layers and the lubricity of their movement which contributes greatly to the tactile simulation of human tissue. Present in the prosthesis is a ballast lumen which moves freely and contributes mass and motility to the prosthesis. The prosthesis finds ready use in the augmentation or restructuring of the human breast as well as in cosmetic modification of other portions of the anatomy as, for example, the chin, the pectorals, the calf muscles, etc.

Those skilled in the art will conceive of other embodiments of the invention which may be drawn from the disclosure herein. To the extent that such other embodiments are so drawn, it is intended that they shall fall within the ambit of protection provided by the claims herein.

Having described the invention in the foregoing description and drawings in such clear and concise manner that those skilled in the art may readily understand and practice the invention, that which is claimed is:

1. A multiple lumen prosthesis comprising:
   a first, ballast lumen;
   a second lumen enclosing said ballast lumen;
   each said lumen having flexible exterior and interior walls, said interior walls defining an interior void, said ballast lumen being enclosed within said interior void of said second lumen;
   a first thin coating of lubricant on the interior walls of said second lumen;
   a second thin coating of lubricant on the exterior walls of said ballast lumen; said first coating and said second coating of lubricant being insufficient in quantity of lubricant contained therein to inflate said second lumen and of a volume selected to provide a thin coating of lubricant sufficient for inhibiting direct contact of said exterior walls of said ballast lumen with said interior walls of said second lumen; and
   means coupling said first and second coatings of lubricant for renewing said first and said second coatings of lubricant by redistributing lubricant within said first and said second coatings, said means for renewing said first and said second coatings of lubricant comprises an interstitial, distribution layer of lubricant, immiscible in said first and said second coatings of lubricant, said distribution layer of lubricant being generally located between said first and said second coatings of lubricant, further inhibiting direct contact of said exterior walls of said ballast lumen with said interior walls of said second lumen, and redistributing lubricant in said first and second coatings of lubricant along boundaries at which said distribution layer of lubricant moves relative to said first and said second coatings.

2. The prosthesis of claim 1 wherein said means for renewing said first and said second coatings of lubricant comprises said ballast lumen;

said ballast lumen having its said interior void filled with fluid of a selected density, said ballast lumen being freely movable within said interior void of said second lumen, the free movement of said ballast lumen within said second lumen bringing said first and said second coatings of lubricant into repeated, moving contact whereby lubricant within said first and said second coatings is exchanged and redistributed.

3. The prosthesis of claim 2 wherein said flexible interior and exterior walls of said first and said second lumens are hereinafter denoted tissue simulating walls and comprise a material selected, in combination with the multiplicity of said walls and the lubricity of relative motion among said walls, to impart the tactility and movement of natural body tissue when said prosthesis is implanted in a patient's body, said relative motion being induced, in part, by movement of said ballast lumen within said second lumen.

4. The prosthesis of claim 3 further comprising a multiplicity of additional lumens, third through N, where N represents a selected maximum number of lumens comprising said prosthesis, each of said third through N lumens having flexible exterior and interior walls defining an interior void in each of said lumens;

said interior walls of said third through N lumens having a said first coating of lubricant thereon;

said exterior walls of said second through (N−1) lumens having a said second coating of lubricant thereon;

each said third through N lumens being graduated in size to accept, and accepting, its preceding one of said second through (N−1) lumens within its said interior void, the size gradation being sufficient to permit free relative motion between the interior walls of a given one of said third through N lumens and the exterior walls of its preceding one of said second through (N−1) lumens enclosed within said interior void of said given one of said lumens, said prosthesis being a sac-en-sac assembly of said first through N lumens.

5. The prosthesis of claim 4 further comprising means coupling said first and said second coatings of lubricant between adjacent interior and exterior walls of said multiplicity of additional lumens for renewing said first and said second coatings.

6. The prosthesis of claim 5 wherein said means for renewing said first and said second coating of lubricants comprises said adjacent interior and exterior walls of said multiplicity of additional lumens, said free relative motion between said walls bringing said first and said second coating of lubricant into repeated, moving contact whereby lubricant within said first and said second coatings is exchanged and redistributed.

7. The prosthesis of claim 6 wherein said means for renewing said first and said second coatings of lubricant further comprises an interstitial, distribution layer of lubricant, immiscible in said first and said second coatings of lubricant, said distribution layer of lubricant being generally located between said first and said second coatings of lubricant, further inhibiting direct contact of said exterior walls of said ballast lumen with said interior walls of said second lumen, and redistributing lubricant in said first and said second coatings of lubricant along boundaries at which said distribution layer of lubricant moves relative to said first and said second coatings.

8. The prosthesis of claim 3 further comprising a plurality of tissue simulating walls each coupled to a first wall of said second lumen;

each one of said plurality of tissue simulating walls being concentric, one to the other;

said tissue simulating walls being graduated in size;

each one of said tissue simulating walls, so coupled to said second lumen, defining an interior void; and each one of said tissue simulating walls having thereon at least one of said first and said second coatings of lubricant for inhibiting direct contact between adjacent said tissue simulating walls within each said interior void so defined.

9. The prosthesis of claim 8 further comprising means coupled to each of said at least one of said first and said second coatings of lubricant for redistributing lubricant on said tissue simulating walls.

10. The prosthesis of claim 9 wherein said means for redistributing lubricant on said tissue simulating walls comprises said ballast lumen, the free movement of said ballast lumen within said second lumen communicating motion to said tissue simulating walls whereby said lubricant coatings are brought into repeated moving contact whereby lubricant within said lubricant coatings is exchanged and redistributed.

11. The prosthesis of claim 1 wherein said flexible interior and exterior walls of said first and said second lumens comprise a material selected, in combination with the multiplicity of said walls and the lubricity of relative motion among said walls, to impart the tactility and movement of natural body tissue when said prosthesis is implanted in a patient's body, said relative motion being induced, in part, by movement of said ballast lumen within said second lumen.

12. The prosthesis of claim 11 further comprising a multiplicity of additional lumens, third through N, where N represents a selected maximum number of lumens comprising said prosthesis, each of said third through N lumens having flexible exterior and interior walls defining an interior void in each of said lumens;

said interior walls of said third through N lumens having a said first coating of lubricant thereon;

said exterior walls of said second through (N−1) lumens having a said second coating of lubricant thereon;

each said third through N lumens being graduated in size to accept, and accepting, its preceding one of said second through (N−1) lumens within its said interior void, the size gradation being sufficient to permit free relative motion between the interior walls of a given one of said third through N lumens and the exterior walls of its preceding one of said second through (N−1) lumens enclosed within said interior void of said given one of said lumens, said prosthesis being a sac-en-sac assembly of said first through N lumens.

13. The prosthesis of claim 12 further comprising means coupling said first and said second coatings of lubricant between adjacent interior and exterior walls of said multiplicity of additional lumens for renewing said first and said second coatings.

14. The prosthesis of claim 13 wherein said means for renewing said first and said second coating of lubricants comprises said adjacent interior and exterior walls of said multiplicity of additional lumens, said free relative motion between said walls bringing said first and said second coating of lubricant into repeated, moving contact whereby lubricant within said first and said second coatings is exchanged and redistributed.

15. The prosthesis of claim 14 wherein said means for renewing said first and said second coatings of lubricant comprises said ballast lumen;
said ballast lumen having its said interior void filled with fluid of a selected density,
said ballast lumen being freely movable within said interior void of said second lumen, the free movement of said ballast lumen within said second lumen bringing said first and said second coatings of lubricant into repeated, moving contact whereby lubricant within said first and said second coatings is exchanged and redistributed.

16. The prosthesis of claim 11 wherein said means for renewing said first and said second coatings of lubricant comprises said ballast lumen;
said ballast lumen having its said interior void filled with fluid of a selected density,
said ballast lumen being freely movable within said interior void of said second lumen, the free movement of said ballast lumen within said second lumen bringing said first and said second coatings of lubricant into repeated, moving contact whereby lubricant within said first and said second coatings is exchanged and redistributed.

17. The prosthesis of claim 11 further comprising a plurality of tissue simulating walls each coupled to a first wall of said second lumen;
each one of said plurality of tissue simulating walls being concentric, one to the other;
said tissue simulating walls being graduated in size;
each one of said tissue simulating walls, so coupled to said second lumen, defining an interior void; and
each one of said tissue simulating walls having thereon at least one of said first and said second coatings of lubricant for inhibiting direct contact between adjacent said tissue simulating walls within each said interior void so defined.

18. The prosthesis of claim 17 further comprising means coupled to each of said at least one of said first and said second coatings of lubricant for redistributing lubricant on said tissue simulating walls.

19. The prosthesis of claim 18 wherein said means for renewing said first and said second coatings of lubricant comprises said ballast lumen;
said ballast lumen having its said interior void filled with fluid of a selected density,
said ballast lumen being freely movable within said interior void of said second lumen, the free movement of said ballast lumen within said second lumen bringing said first and said second coatings of lubricant into repeated, moving contact whereby lubricant within said first and said second coatings is exchanged and redistributed.

20. The prosthesis of claim 19 wherein said means for redistributing lubricant on said tissue simulating walls comprises said ballast lumen, the free movement of said ballast lumen within said second lumen communicating motion to said tissue simulating walls whereby said lubricant coatings are brought into repeated moving contact whereby lubricant within said lubricant coatings is exchanged and redistributed.

21. The prosthesis of claim 1 wherein said means for renewing said first and said second coatings of lubricant comprises said ballast lumen;
said ballast lumen having its said interior void filled with fluid of a selected density,
said ballast lumen being freely movable within said interior void of said second lumen, the free movement of said ballast lumen within said second lumen moving said second coating of lubricant relative to said first coating of lubricant whereby lubricant within said first and said second coatings is exchanged and redistributed.

22. The prosthesis of claim 1 further comprising a plurality of tissue simulating walls each coupled to a first wall of said second lumen;
each one of said plurality of tissue simulating walls being concentric, one to the other;
said tissue simulating walls being graduated in size;
each one of said tissue simulating walls, so coupled to said second lumen, defining an interior void; and
each one of said tissue simulating walls having thereon at least one of said first and said second coatings of lubricant for inhibiting direct contact between adjacent said tissue simulating walls within each said interior void so defined.

23. A multiple lumen prosthesis comprising:
a first, ballast lumen;
a second lumen enclosing said ballast lumen;
each said lumen having flexible exterior and interior walls, said interior walls defining an interior void, said ballast lumen being enclosed within said interior void of said second lumen;
a first thin coating of lubricant on the interior walls of said second lumen;
a second thin coating of lubricant on the exterior walls of said ballast lumen; said first coating and said second coating of lubricant being insufficient in quantity of lubricant contained therein to inflate said second lumen and of a volume selected to provide a thin coating of lubricant sufficient for inhibiting direct contact of said exterior walls of said ballast lumen with said interior walls of said second lumen;
means coupling said first and second coatings of lubricant for renewing said first and said second coatings of lubricant by redistributing lubricant within said first and said second coatings;
said means for renewing said first and said second coatings of lubricant comprises said ballast lumen;
said ballast lumen having its said interior void filled with fluid of a selected density,
said ballast lumen being freely movable within said interior void of said second lumen, the free movement of said ballast lumen within said second lumen bringing said first and said second coatings of lubricant into repeated, moving contact whereby lubricant within said first and said second coatings is exchanged and redistributed; and said flexible interior and exterior walls of said first and said second lumens comprise a material selected, in combination with the multiplicity of said walls and the lubricity of relative motion among said walls, to impart the tactility and movement of natural body tissue when said prosthesis is implanted in a patient's body, said relative motion being induced, in part, by movement of said ballast lumen within said second lumen; and said means for renewing said first and said second coatings of lubricant further comprises an interstitial, distribution layer of lubricant, immiscible in said first and said second coatings of lubricant, said distribution layer of lubricant being generally located between said first and said second coatings of lubricant, further inhibiting direct contact of said exterior walls of said ballast lumen with said interior walls of said second lumen, and redistributing lubricant in said first and second coatings of lubricant along boundaries at which said distribution layer of lubricant moves relative to said first and said second coatings.

24. The prosthesis of claim 23 further comprising a multiplicity of additional lumens, each of said additional lumens having flexible exterior and interior walls defining an interior void in each of said additional lumens;

said interior walls of said additional lumens having a non-inflating volume of said first coating of lubricant thereon;

said exterior walls of all said second through a last one of said additional lumens having a non-inflating volume of said second coating of lubricant thereon;

each of said additional lumens being graduated in size to accept, and accepting, its preceding one of said second through a next-to-the-last one of said additional lumens within its said interior void, the size gradation being sufficient to permit free relative motion between the interior walls of a given one of said additional lumens and the exterior walls of its preceding one of said second through said next-to-the-last one of said additional lumens enclosed within said interior void of said given one of said additional lumens, said prosthesis being a sac-en-sac assembly of said first through said last one of said additional lumens.

* * * * *